US005344981A

United States Patent [19]

Hendricks

[11] Patent Number: 5,344,981
[45] Date of Patent: Sep. 6, 1994

[54] FLUORINATED MONOMERS USEFUL FOR PREPARING FLUORINATED POLYQUINOLINE POLYMERS

[75] Inventor: Neil H. Hendricks, Brea, Calif.

[73] Assignee: Maxdem Incorporated, San Dimas, Calif.

[21] Appl. No.: 98,197

[22] Filed: Jul. 28, 1993

Related U.S. Application Data

[60] Division of Ser. No. 744,539, Aug. 13, 1991, Pat. No. 5,247,050, which is a continuation-in-part of Ser. No. 568,059, Aug. 16, 1990, abandoned.

[51] Int. Cl.$^5$ .................. C07C 225/22; C07C 49/76; C07C 49/784; C07C 49/84
[52] U.S. Cl. .................................. 564/328; 568/331; 568/332; 568/333
[58] Field of Search ............... 564/328; 568/331, 332, 568/333

[56] References Cited

U.S. PATENT DOCUMENTS

| | | | |
|---|---|---|---|
| 4,000,187 | 12/1976 | Stille | 260/50 |
| 4,111,906 | 9/1978 | Jones et al. | 528/229 |
| 4,159,251 | 7/1979 | Wrasidlo et al. | 210/321 |
| 4,203,922 | 5/1980 | Jones et al. | 260/570 |
| 4,507,462 | 3/1985 | Stille | 528/125 |
| 4,649,207 | 5/1987 | Lau et al. | 549/563 |
| 4,722,985 | 2/1988 | Lau et al. | 526/245 |
| 5,017,577 | 5/1991 | Stille | 528/125 |
| 5,166,365 | 11/1992 | Ohsaka et al. | 549/241 |

OTHER PUBLICATIONS

St. Clair, A. K., et al, "Low Dielectric Polyimides for Electronic Applications" Paper presented at the National Meeting of the American Chemical Society, Sep. 25-30, 1988, Los Angeles, Calif.

Jones, R. J., et al, "Thermal Properties of EYMYD Polyimides," SAMPE Journal, vol. 25, No. 2, Mar.-/Apr. 1989.

(List continued on next page.)

Primary Examiner—Richard L. Raymond
Attorney, Agent, or Firm—Christie, Parker & Hale

[57] ABSTRACT

A new class of polymers is provided, as well as the monomers used for their preparation. The polymers provided in accordance with practice of the present invention include repeating units comprising one or more quinoline groups, wherein at least a portion of the repeating units includes a hexafluoroisopropylidene (6F) group or a 1-aryl-2,2,2-trifluoroethylidene (3F) group, or both.

The hexafluoroisopropylidene group is referred to herein as a "6F" group and has the following structure:

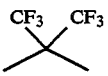

The "6F" group includes a tetravalent carbon atom bound to two trifluoromethyl moieties, with its other two bonds forming linkages in the polymer chain.

The 1-aryl-2,2,2-trifluoroethylidene group is referred to herein as a "3F" group and has the following structure:

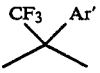

wherein Ar40 is an aryl group.

6 Claims, 3 Drawing Sheets

OTHER PUBLICATIONS

Ruiz L. M., et al, "Fluorinated Polyimide Low Dielectric Coatings," Paper presented at the 1989 International SAMPE Electronics Conference.

Stille, J. K., "Polyquinolines," Macromolecules 1981, vol. 14, 870-880.

Beever, W. H., et al, "Synthesis and Thermal Properties of Aromatic Polymers Containing 3,6-Quinoline Units in the Main Chain," Macromolecules, vol. 12, No. 6, Nov.-Dec. 1979.

Paper prepared by Cassidy, P. E., et al, "Polymers Derived from Hexafluoroacetone," Department of Chemistry, Southest Texas State University; 1988.

Maruyama, Y., et al, "Synthesis and Properties of Fluorine-Containing Aromatic Polybenzoxazoles from Bis(o-aminophenols) and Aromatic Diacid Chlorides by the Silylation Method," Macromolecules, vol. 21, No. 8, Aug. 1988.

Hendricks, N. H., et al, "Thermally Stable, Low Dielectric Polyquinolines for Aerospace and Electronics Applications," Paper presented Jun. 14, 1990, 4th International SAMPE Electronics Conference, Albuquerque, N.M.

Bottino, F. A., et al, "Perfluoroalkylene-Linked Polyquinolines and Related Model Compounds," *Macromolecules,* 15, 227-230 (1982).

FLUORINATED MONOMERS USEFUL FOR PREPARING FLUORINATED POLYQUINOLINE POLYMERS

This application is a division of U.S. Ser. No. 07/744,539, filed Aug. 13, 1991, now U.S. Pat. No. 5,247,050, which was a continuation-in-part of U.S. Ser. No. 07/568,059, filed Aug. 16, 1990, now abandoned.

RELATED APPLICATION

This application is a division of U.S.S.N. 07/744,539, filed Aug. 13, 1991, now U.S. Pat. No. 5,247,050, which was a continuation-in-part of U.S.S.N. 07/568,059, filed Aug. 16, 1990, now abandoned.

FIELD OF THE INVENTION

The present invention relates to a new class of polymers, namely fluorinated quinoline polymers, and the monomers useful for their preparation.

BACKGROUND OF THE INVENTION

New high performance polymers characterized by high strength, resistance to various types of radiation, superior electrical properties, minimal influence of exposure to hot/wet conditions on electrical properties, solubility in common organic solvents, high glass transition temperatures, low densities, low moisture absorption, high thermal and thermooxidative stability and optical transparency are needed as refractive films and coatings. Such materials will also be useful for high density microelectronics packaging applications including their use as interlevel planarizers and as low observable coatings, cable wraps, wire coatings, and thin film capacitors.

Current state-of-the-art, high performance polymers do not possess the combination of properties desired for many aerospace and electronics applications, among others. Polyimides, for example, because of their outstanding thermal stability, have been used as high performance films for a variety of the above-described applications. However, certain desirable combinations of the properties discussed above are not readily attainable with polyimides. The imide moiety, which is relatively polar, tends to absorb unacceptable quantities of moisture for certain applications. In addition polarizability of the imide moiety is likely responsible for the relatively high dielectric constants measured for most polyimides. While chemical modifications such as the incorporation of fluorine into polyimides simultaneously reduces their tendency to absorb moisture and their dielectric constants, other properties such as mechanical strength may be compromised. Moreover, even the incorporation of large quantities of fluorine into the polyamide structure does not reduce the influence of hot/wet conditions on key electrical properties to a desirable extent.

Incorporation of fluorine into other classes of polymers, for example into polyesters, has led to improvements in key properties such as thermal stability, solubility, and dielectric constant; however, as with polyimides, the fluorinated polyesters are not ideally suited for use in highly demanding electronics applications. Due to the polar nature of the ester moiety, these polymers exhibit relatively high dielectric constants and moisture absorption characteristics. Similar considerations apply when considering the incorporation of fluorine into polyamides, polycarbonates, and polybenzimidazoles.

Fluorine has also been incorporated into polybenzoxazoles. Unlike polyimides and other carbonyl-containing polymers, non-fluorinated polybenzoxazoles exhibit relatively low dielectric constants and moisture absorption. However, these polymers suffer from poor solubility in common organic solvents. Although the incorporation of fluorine increases the thermal stability and lowers both moisture absorption and the dielectric constant of these polymers, they still exhibit poor solubility in non-chlorinated, non-phenolic, (e.g, low toxicity), organic solvents suitable, for example, in microelectronics processing.

Therefore, new polymers which, when compared to polyimides and other high performance polymers, possess different combinations of the properties discussed above are needed.

SUMMARY OF THE INVENTION

Polymers are provided in accordance with practice of the present invention which include repeating units comprising one or more quinoline groups wherein at least a portion of the repeating units include a hexafluoroisopropylidene (6F) group or a 1-aryl-2,2,2-trifluoroethylidine (3F) group or both.

The hexafluoroisopropylidene group is referred to herein as a "6F" group and has the following structure:

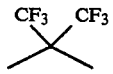

A 6F group includes a tetravalent carbon atom bound to two trifluoromethyl moieties with its other two bonds forming linkages in the polymer chain.

The 1-aryl-2,2,2- trifluoroethylidene group is referred to herein as a "3F" group and has the following structure:

wherein Ar' is an aryl group.

The "3F" group comprises a tetravalent carbon atom bound to one trifluoromethyl moiety and one aryl group with its other two bonds forming linkages in the polymer chain.

The quinoline polymers of the present invention with incorporated trifluoromethyl groups, retain, and in some cases, exceed the thermal stability normally associated with prior art quinoline polymers. The polymers of the present invention are generally more soluble in common organic solvents than are previously described quinoline polymers, they have lower dielectric constants, possess significantly lower moisture absorption characteristics and exhibit smaller increases in dielectric constants when exposed to elevated temperature and humidity.

The polymers provided in accordance with the present invention are particularly suitable for use as thermally stable laminating resins, erosion barrier coatings, corrosion resistant coatings, thermal protective coatings, interlevel planarizers and related electronics applications, reduced observability coatings, composite matrix resins and solid film lubricants and fibers.

The monomers of the present invention, alone or combined with other monomers, are used to prepare the above-described novel polymers.

BRIEF DESCRIPTION OF THE DRAWINGS

These and other features, aspects and advantages of the present invention will be more fully understood when considered with respect to the following detailed description, appended claims, and accompanying drawings, wherein:

DETAILED DESCRIPTION

Figure 1:
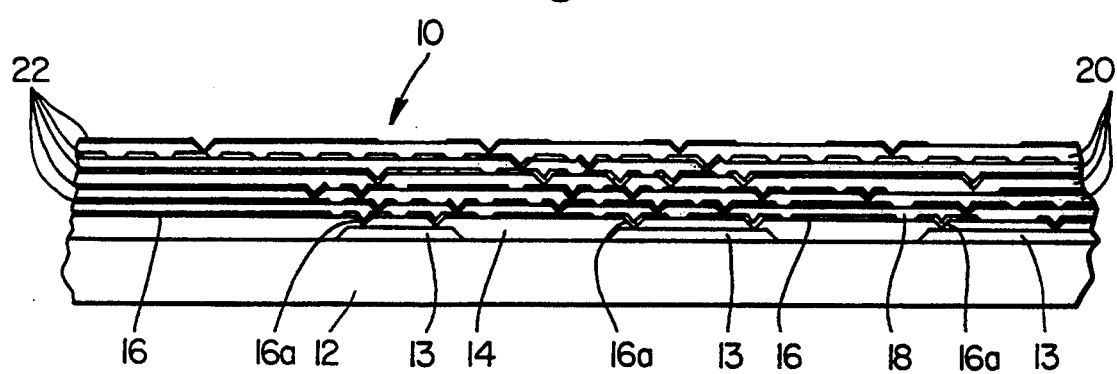
FIG. 1 is a semi-schematic fragmentary cross sectional side view of a multi-chip module provided in accordance with practice of the present invention.

This invention is directed to a new class of polyquinoline polymers and to the novel monomers which are used for their preparation. The polymers provided in accordance with practice of the present invention can be prepared from various combinations of the new monomers and from previously described monomers using the methods for preparing polyquinolines that are described in U.S. Pat. No. 4,000,187 which issued Dec. 28, 1976. U.S. Pat. No. 4,000,187 is incorporated herein by this reference.

The polymers of the present invention comprise quinoline and one or more hexafluoroisopropylidene (6F) and/or 1-aryl-2,2,2- trifluoroethylidene (3F) groups. The "6F" group has the following structure:

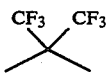

The "6F" group includes a tetravalent carbon atom bound to two trifluoromethyl moieties with its other two bonds forming linkages in the polymer chain;

The "3F" group has the following structure:

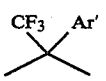

The "3F" group comprises a tetravalent carbon atom bound to one trifluoromethyl moiety and one aryl (Ar') group with its other two bonds forming linkages in the polymer chain.

In one embodiment, the polymer of the present invention incorporates repeating units which have the general structure:

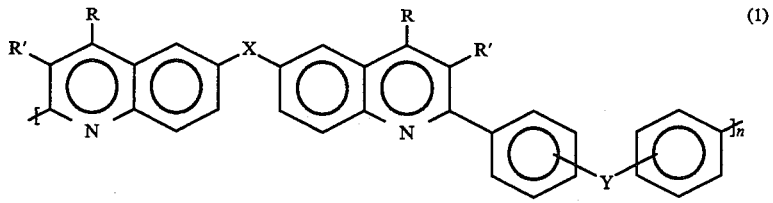
(1)

wherein R and R' are independently hydrogen or aryl, and wherein each of the R and R' groups can be the same or different, and X and Y are divalent radicals, at least one of which contains either a hexafluoroisopropylidene (6F) group:

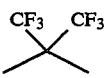

or a 1-aryl-2,2,2,-tridluoroethylidene (3F) group:

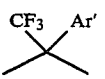

wherein Y is —G— and X is —G— or —Ar—G—Ar—, wherein X and Y can be the same or different, where —G— is a divalent radical taken from the group: nil, —O—, —N(H)—, —S—,

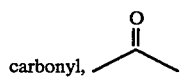

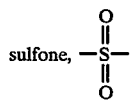

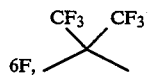

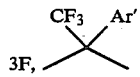

hexafluoroisopropylidene diphenoxy,

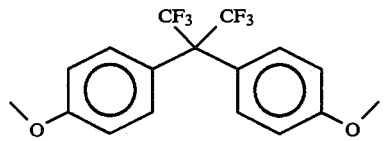

1-aryl-2,2,2-trifluoroethylidene diphenoxy,

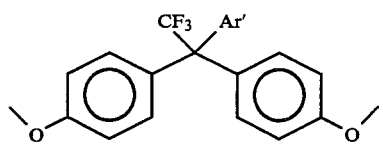

-continued phenylene, and 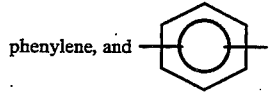

Phenylenedioxy 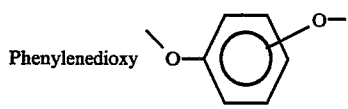

wherein Ar' is an aryl group including but not limited to phenyl, tolyl, naphthyl, biphenyl, phenoxyphenyl, and trifluoromethylphenyl, and wherein Ar is a divalent aromatic group including, but not limited to:

phenylene, 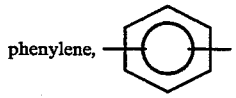

biphenylene, 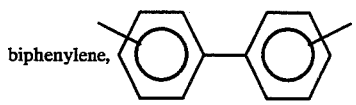

naphthyleneyl, 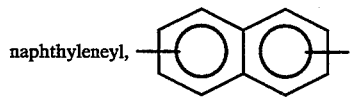

diphenylether, 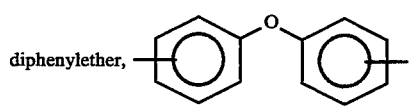

diphenylketone, 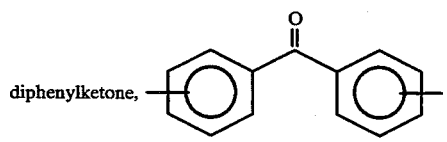

pyridyl, 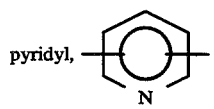

-continued bipyridyl 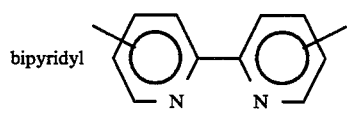

quinolyl, 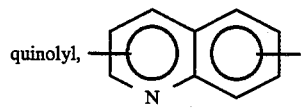

diphenylsulfide, 

diphenylsulfone, 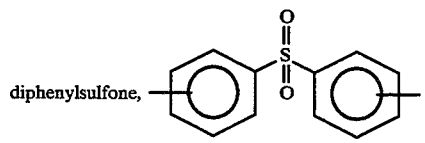

and n is an integer and is equal to the number of repeating units in the polymer chain.

In another exemplary embodiment, the polymer of the present invention has repeating units of the following general structure:

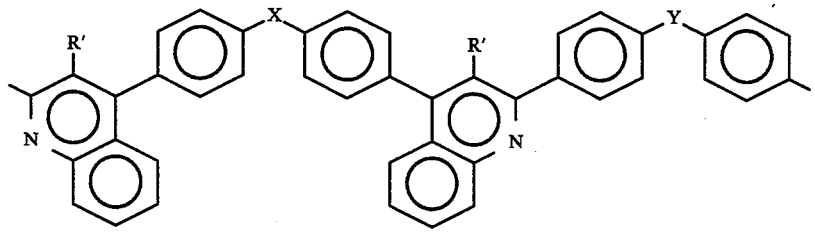 (2)

wherein R', X and Y are as defined above.

In yet another exemplary embodiment, the polymer of the present invention has repeating units of the following general structure:

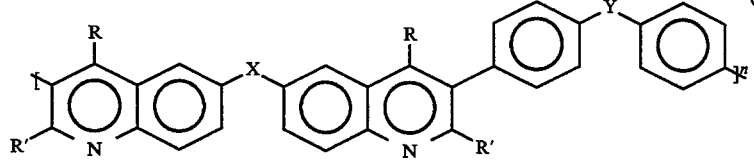 (3)

wherein R, R', X and Y are as defined above.

In yet another exemplary embodiment, the polymer of the present invention has the repeating units of the following general structure:

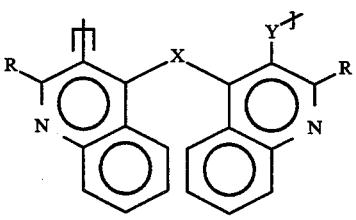 (4)

wherein R, X and Y are as defined above.

In yet another exemplary embodiment, the polymer of the present invention has repeating units of the following general structure:

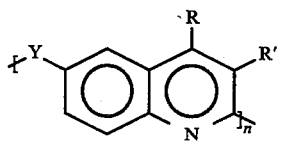 (5)

wherein R, R' and Y are as defined above.

In more particular embodiments of the structure (5), R and R' are independently hydrogen or phenyl and Y is selected from the group:

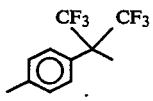 (6)

and

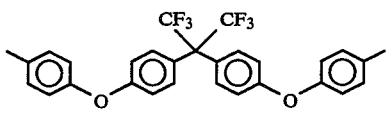 (7)

The polymer compositions of the present invention may have varying percentages by weight of quinoline groups and 6F and/or 3F groups. The actual percent will depend on the particular monomers utilized. For example, in the polymer of structure (1), if X is hexafluoroisopropylidene diphenoxy, Y is diphenylether, R and R' are phenyl, the weight fraction of quinoline is 21.3% and the weight fraction of fluorine is 9.7%. The weight fraction of quinoline will be preferably about 10% or greater and the weight fraction of fluorine will preferably be about 1% or greater.

Polymers of the present invention which contain relatively small amounts of fluorine, for example between 1% and 5%, are attractive in that they exhibit many of the desirable properties which are generally characteristic of the polymers of the present invention. For example, the incorporation of small amounts of fluorine via 3F and 6F groups favorably impacts the solubility of the polymers, thus enhancing their utility.

The polymer compositions of the present invention are generally useful in the area of electronics and microelectronics applications because of their combination of low dielectric constant, low water uptake, high thermal stability and good solubility. The instant polymers are useful for dielectric layers in integrated circuits (IC's) such as planarizers, insulators, passivation layers, encapsulants, adhesives and the like. They are also useful in various wiring board applications, such as printed wiring boards, flexible wiring boards, tape automated bonding substrates, multi-chip modules dielectrics and the like. They may also be used in fabrication of electronic components such as capacitors, resistors, discrete semiconductor devices, inductors, or other devices requiring an insulating layer.

The polymers of the present invention are also useful in electrical applications such as wire coatings and insulation, insulating lacquers, for fabricating molded connectors, switches, enclosures, insulating strips, or the like. Other applications requiring low dielectric constant and good mechanical properties are radomes, space based applications including protective coatings, low observable applications and the like. The polymers of the present invention are also useful as matrix resins for composites.

The instant polymers may also be used as free standing films, as laminated films, fibers, coatings or with other processing methods commonly used for polymers.

PREPARATION OF MONOMERS USED TO PREPARE THE POLYMERS OF THE PRESENT INVENTION

Many of the polymers which are the subject of the present invention result from reacting certain previously known monomers with new monomers which are described herein. The monomers which are previously known include various bis(aminoketones) and bis(-ketomethylene) compounds, many of which are described in the above mentioned U.S. Pat. No. 4,000,187; and in U.S. Pat. No. 5,017,677 which issued May 21, 1991 as well as in the chemical literature, for example, by Stille, et al., in the following volumes of *Macromolecules*: Vol. 9, 489 (1976); Vol. 9,496 (1976); Vol. 12, p. 1036 (1979); Vol. 14, p. 494 (1981). The disclosures of the foregoing *Macromolecules* volumes and U.S. Pat. No. 5,017,677 are incorporated herein by this reference.

More generally, bis(ketomethylene) compounds (R'H$_2$C(CO)Y(CO)CH$_2$R'-where R' and Y are as described above) which can be used to prepare polymers of the present invention, can be synthesized as follows:

In the cases where G is nil, —O—, —N(H)—, —S—, 6F or 3F and Ar is phenyl, biphenyl, naphthyl, pyridyl, bipyridyl, diphenyl ether, and diphenyl sulfide, it is known in the art that diacetyl compounds of the type R'H$_2$C(CO)ArGAr(CO)CH$_2$R'

can be prepared by acylation of Ar—G—Ar with acetyl chloride under Freidel-Crafts conditions. Where R' is not hydrogen, but, for example phenyl, acylation can be effected with substituted acid chlorides, for example phenacetyl chloride.

In the cases where Ar is diphenyl ketone, diphenyl sulfone, or other substrates that are not sufficiently reactive to undergo acylation, an alternative approach must be used. For example, if G is —O—, diphenyl ether can be diacylated using the acid chloride of the corresponding acetyl, benzoyl, or other appropriately substituted benzoic acid:

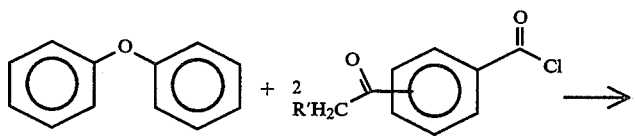

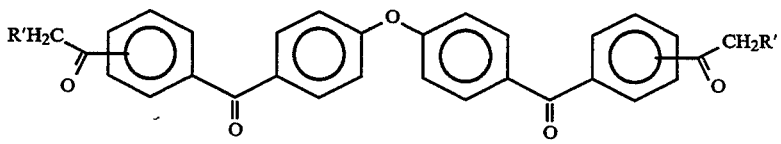

10

Similarly, for the cases where G is -S- or -N(H)-, diphenyl sulfide and diphenyl amine respectively may be used in the above-described scheme in place of diphenyl ether.

It is known in the art that an alternative method for forming bis(ketomethylene) compounds R'H₂C(CO)ArGAr(CO)CH₂R' involves condensation reactions, where compounds of the type

Ar-GH are condensed with compounds of the type

Z-Ar where Z is an appropriate leaving group, such as halogen or nitro, under basic conditions. For example, in the case where Ar is phenyl and G is —O—, hydroxyacetophenone may be condensed with fluoroacetophenone to form 4,4'-diacetyl diphenyl ether.

Specific, nonlimiting examples of the preparation of diacetyl compounds which can be used to prepare polymers of the present invention where G is 6F are provided as Examples 1 and 2 below.

The synthesis of bis(aminoketone) compounds are described by Stille, et al., in the previously listed volumes of *Macromolecules* and in U.S. Pat. Nos. 4,000,187 and 5,017,677. The synthesis procedures set forth by Stille, et al. can be used to prepare the bis-(aminoketone) monomers of the present invention.

More generally, bis(aminoketones) of the formula:

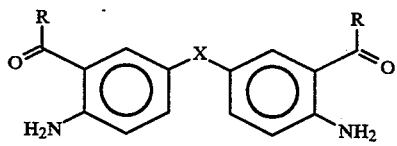 (8)

where X is as previously defined can be prepared as follows:

In the cases where X is nil, —O—, —N(H)—, —S—, 3F or 6F, it is known in the art that nitration techniques can be used to prepare dinitro compounds of the formula:

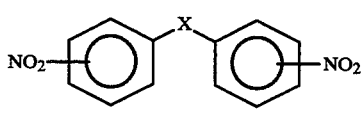 (9)

For example, in the case where X is —O—, nitration of diphenyl ether leads to 4,4-dinitrodiphenyl ether. It is known that dinitro compounds of formula (9) can be condensed under basic conditions with phenylacetonitrile to yield the corresponding benzisoxazole (sometimes called anthranil) compounds.

Alternatively, the required dinitro compounds can be prepared by condensation reactions. For example, in the case where X is —O—, dinitrodiphenyl ether may be prepared by condensing 4-nitrophenol with 4- fluoronitrobenzene under basic conditions. In the case where X is —S—, dinitrothiophenyl ether may be similarly prepared.

Other examples of the required dinitro compounds can be prepared by homocoupling of iodo (or bromo) nitroaromatic compounds such as 4-iodonitrobenzene. Compounds such as this can be coupled through the halogen atoms using the Ullmann reaction (or modifications thereof) to yield 4,4'-dinitrobiphenyl. Subsequent condensation with phenylacetonitrile followed by reduction with hydrogen using palladium on carbon as catalyst leads to the bis(aminoketone) wherein X is nil. Similar chemistry can be used to prepare other bis-(aminoketones).

A bis(aminoketone) of the formula (8), wherein X is 6F, can be prepared as follows: starting with 2,2'-bis(4-phenyl) hexafluoropropane (obtained by first treating commercially available 4,4'-(hexafluoroisopropylidene) diphenol with phosphorous tribromide followed by formation of a di-Grignard reagent and then quenching in water), nitration under standard conditions leads to 2,2'-(4-nitrophenyl) hexafluoropropane. This compound can be treated with phenylacetonitrile under basic conditions followed by reduction to yield the bis (aminoketone) of the structure (10) shown below.

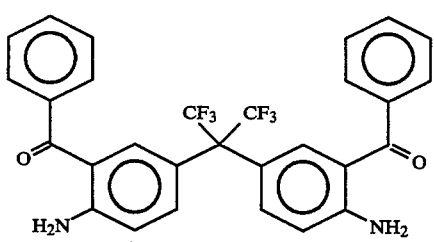 (10)

A second bis(aminoketone) wherein X is hexafluoroisopropylidene diphenoxy can be prepared by condensing 4,4'-(hexafluoroisopropylidene)diphenol with two equivalents of 4-fluoronitrobenzene under basic conditions to yield the corresponding dinitro compound. Treatment of this dinitro compound with phenyl acetonitrile under basic conditions followed by reduction yields the bis(aminoketone) of the structure (11) shown below.

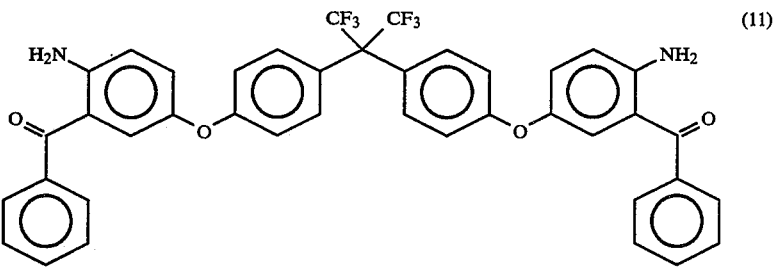

(11)

In addition to preparing polymers of the present invention through the condensation of bis(ketomethylene) and bis(aminoketone) compounds (e.g., difunctional monomers known in the art as "AA" and "BB" monomers), other, distinct polymers of the present invention can be prepared from "AB" monomers. In order to prepare polymers of the present invention with an "AB" monomer, the monomer must contain a ketomethylene group, an aminoketone group, and either 6F or a 3F group or both. Examples of AB monomers are as follows (Although the monomers are shown with 6F groups, 3F groups could be substituted):

aniline in a one-to-one ratio, followed by protection of the amino group with benzoyl chloride. A second condensation of the intermediate "6F"-containing hydroxy compound with ethyl benzene followed by oxidation to the methyl ketone, and finally a Fries rearrangement on the benzamide leads to the "AB" monomer.

Monomers containing the 3F group can be prepared analogously to the above 6F monomers.

Detailed procedures for preparing certain 6F-containing monomers required to prepare the polymers of the present invention are set forth in Examples 1-3 which follow. The Examples are for illustrative pur-

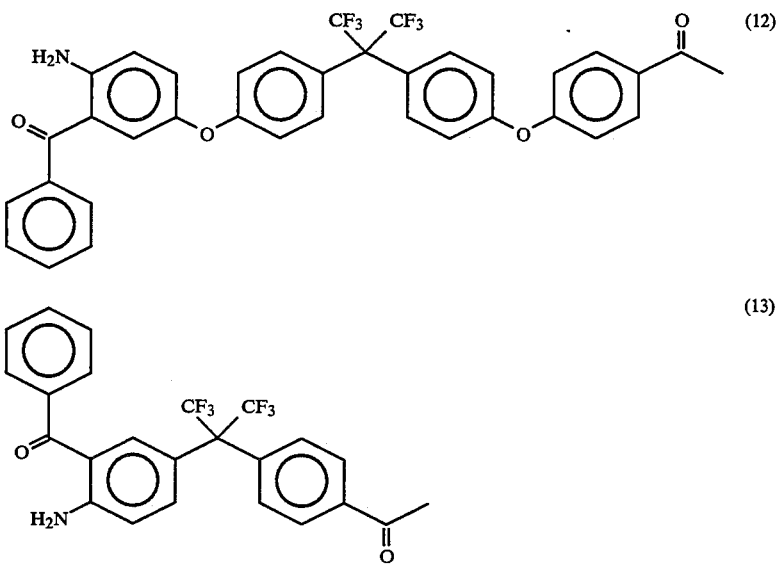

The monomer of formula (12) can be prepared by condensing hexafluoroisopropylidene diphenol with 4-fluoroacetophenone in a one-to-one ratio, followed by protection of the acetyl group with 2-methoxy propene. A second condensation of the intermediate 6F-containing phenol with chloronitrobenzene under basic conditions followed by condensation of the pendant nitro group with phenylacetonitrile leads to the intermediate anthranil (benzisoxazole). The monomer is obtained by reducing the anthranil to the ortho aminoketone and finally deprotecting by removing 2-methoxy propene with aqueous acid.

The monomer of formula (13) can be prepared by first condensing commercial hexafluoroacetone with poses and are not to be considered to limit the invention in any way.

EXAMPLE 1

Preparation of 2,2'-bis[4-(4-acetylphenoxy)phenyl] hexafluoropropane

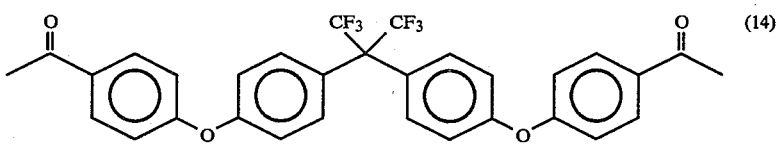

A suspension of 16.9 grams (0.122 moles) anhydrous potassium carbonate in 373 milliliters of N,N'-dimethylacetamide was prepared in a 1 liter, 2- neck round bottom flask equipped with a reflux condensor and a nitrogen gas inlet. To the suspension was added 18.66 grams (0.0555 moles) of commercially obtained 4,4'-

(hexafluoroisopropylidene) diphenol using a powder addition funnel against a counter current of nitrogen gas. The system was purged and stirred under nitrogen for fifteen minutes, as heat was gradually applied via a heating mantle. Next, 20.21 milliliters (0.166 moles, 3 equivalents relative to the diphenol) of commercially obtained 4-fluoroacetophenone was added via a syringe to the heated solution. The solution was refluxed and stirred for 48 hours, at which time no diphenol was evident by thin layer chromatography. The quantity of solvent was reduced to approximately 200 milliliters by distillation, whereupon the solution was cooled, and poured into approximately 500 milliliters of 1 molar HCl. The product precipitated as an off white granular solid. About 10 grams of the crude product were dissolved in dichloromethane and loaded onto a chromatography column using TLC grade silica. The product was obtained in pure form by eluting the column with a mixture of dichloromethane: hexanes in a 4:1 ratio. The structure of 2,2'-bis[4-(4-acetylphenoxy)phenyl]hexafluoropropane was confirmed by proton NMR and elemental analysis. The melting point of the compound was shown to be approximately 134-135° C.

EXAMPLE 2

Preparation of 2,2'-bis(4-acetylphenyl) hexafluoropropane

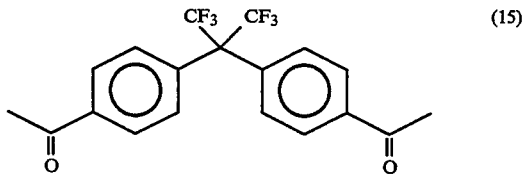

(15)

To an oven-dried, argon purged 15 milliliter round bottom flask, 143 milligrams (5.87×10$^{-3}$ moles) of magnesium turnings were added. Then 1 milliliter of carbon tetrachloride and two milliliters of anhydrous ethanol were added via a syringe needle through a septum. After heating to achieve ..dissolution of the magnesium, 4 milliliters of anhydrous diethyl ether were added via an addition funnel. To this refluxing solution was slowly added, via an addition funnel, a solution consisting of 964 milligrams (5.87×10$^{-3}$ moles) of diethyl malonate (which had previously been purified by distillation), 0.547 milliliters of anhydrous ethanol, and 0.657 milliliters of anhydrous diethyl ether. The reaction mixture was then heated to reflux for three hours.

1.2 milliliters of the diacid chloride derived from 2,2'-bis(carboxyphenyl) hexafluoropropane (obtained from Central Glass and converted to the diacid chloride by refluxing the diacid with excess thionyl chloride in toluene for four hours followed by evaporation of solvent) was dissolved in 3 milliliters of diethyl ether and added to the reaction via an addition funnel. Shortly thereafter, a white precipitate formed, which was removed from the reaction flask and cooled. The white precipitate was placed in a 25 milliliter Erlenmeyer flask and 660 milligrams of sulfuric acid dissolved in 5 milliliters of water was added. The solid dissolved and two liquid (e.g., aqueous and ether) layers formed. The ether layer was separated, and the aqueous layer was extracted with ether. The ether extracts were combined, washed with water, and the ether was removed by evaporation. To the residue was added a solution consisting of 1.6 milliliters of glacial acetic acid, 0.21 milliliters of sulfuric acid and 1.1 milliliters of water. This mixture was refluxed for four hours.- The reaction mixture was then made alkaline with a 20% sodium hydroxide solution, chilled using an ice bath, and extracted with several portions of ether. The combined etheral extracts were washed with water, dried over anhydrous sodium sulfate, and the ether was removed by evaportion. The product 2,2'-bis(4-acetylphenyl) hexafluoropropane was purified by medium pressure (flash) chromatography using TLC grade silica and an eluent consisting of 20% hexanes and 80% dichloromethane. Evaporation of the chromatography solvent yielded pure product, which was characterized by melting point, 1H-NMR and FTIR spectroscopy, and elemental analysis. The purity of the product was determined by reverse phase high pressure liquid chromatography to be 99.43%.

EXAMPLE 3

Preparation of 1,1-bis[4-(4-acetylphenoxy)phenyl]-1-phenyl-2,2,2-trifluoroethane A suspension of 15.2 grams (0.11 moles) anhydrous potassium carbonate in 370 milliliters of N$_2$N'-dimethylacetamide is prepared in a 1 liter, 2-necked round bottom flask equipped with a reflux condensor and a nitrogen gas inlet. To the suspension is added 16.61 grams (0.05 moles) of 1,1-bis-(4-hydroxyphenyl)-1-phenyl-2,2,2-trifluoroethane) using a powder additional funnel against a counter current of nitrogen gas, as heat is gradually applied via a heating mantle. Next 18.26 milliliters (0.15 moles, 3 equivalents relative to the diphenol) of commercially obtained 4- fluoroacetophenone is added via a syringe to the heated solution. The solution is refluxed and stirred for 48 hours, at which time no diphenol is evident by thin layer chromatography (elution with 2:1 hexanes:ethyl acetate). The quantity of solvent is reduced to approximately 200 milliliters by distillation, whereupon the solution is cooled, and poured into approximately 500 milliliters of 1M HCL. The product precipitates as an off white granular solid. About 10 grams of the crude product is dissolved in dichloromethane and loaded onto a chromatography column using TLC grade silica. The product is obtained in pure form by eluting the column with a mixture of dichloromethane:hexanes in a 4:1 ratio.

The preparation of 3,3'-dibenzoyl-4,4' diaminodiphenyl ether and 3,3'-dibenzoyl-4,4'-diaminobiphenyl (also called 3,3'-dibenzoylbenzidine) are well known in the art and are illustrated respectively in Norris, S.O. and Stille, J.K., *Macromolecules*, Vol. 9, 496(1986) and Sybert, P.V. et al., *Macromolecules*, 14, 493 (1981). The aforementioned Macromolecules articles are incorporated herein by this reference.

Copolymers

Since monomers used to prepare polyquinolines which contain 3F or 6F groups are generally more expensive than non-fluorinated monomers, a cost advantage is typically realized by minimizing the number of 3F or 6F groups contained in the new polymers. This is best accomplished by preparing copolymers. Copolymers which are polymers of the present invention may be block copolymers, including diblock copolymers, triblock copolymers, and multiblock copolymers; they may also be random copolymers, or more complicated types of copolymers. Methods for forming polyquinoline copolymers which can be used for producing the novel copolymers of the present invention are set forth in U.S. Pat. No. 5,017,677.

Any combination and any number of bis(ketomethylene) and bis(aminoketone) monomers (BB and AA monomers, respectively, as are described in U.S. Pat. Nos. 4,000,187 and 5,017,677) may be used to prepare copolymers of the present invention, as long as at least one of the monomers contains either a 3F or a 6F group. AB monomers, i.e. those monomers which contain a ketomethylene group on one end and an aminoketone group on the other end, may be used alone or in combination with the AA and BB monomers to provide the copolymers of the present invention.

For example, copolymers provided in accordance with the present invention comprising repeating units which incorporate one or more quinoline groups, can be formed by polymerizing a combination of monomers selected from the group consisting of:

(a) One or more type AA monomers, one or more type BB monomers and one or more type AB monomers;

(b) One or more type AA monomers and one or more type BB monomers, where the total number of different type AA and BB monomers is three or greater; and (c) two or more type AB monomers; wherein at least one of the monomers in each of the combinations (a), (b) and (c) above incorporates a 3F or a 6F group or both.

Both fluorinated and non-fluorinated monomers may be employed in the preparation of copolymers which are polymers of the present invention, with the weight fraction of fluorine ranging from relatively large (e.g., more than 10%) to relatively small (e.g., 1% to 5%).

For example, in yet another exemplary embodiment, the polymer of the present invention incorporates two repeating units randomly dispersed throughout the polymer chain, having the general structure:

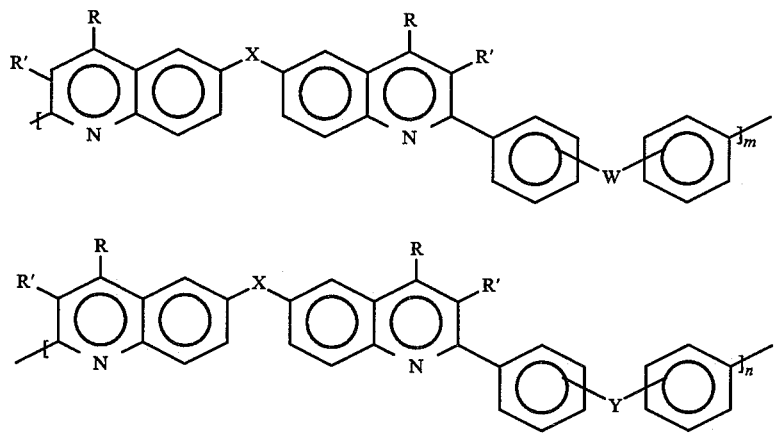

In the general structure (16), which is meant to signify either a random or a block copolymer, X and Y are as previously described, except that Y represents a group which contains either a 3F or a 6F group, and W is a divalent radical selected from nil, —O—, —N(H-), —S—, carbonyl, sulfone and phenylene. The numbers m and n signify the number of repeat units in any given polymer chain.

PREPARATION OF POLYMERS OF THE PRESENT INTENTION

To prepare polymers of the present invention with X and Y as previously defined, the following general procedure is provided:

A bis (ketomethylene) compound (an AA compound) of the following general formula:

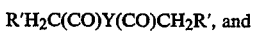

R'H$_2$C(CO)Y(CO)CH$_2$R', and a bis (aminoketone) compound (a BB compound) of the following general formula:

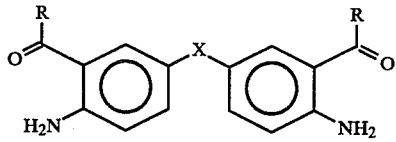

wherein R, R' X and Y are as defined above, are placed in a round bottom flask, resin kettle, or other suitable vessel. Preferably the amounts of AA and BB are equimolar. Diphenyl phosphate, monophenyl phosphate, or mixtures of the two are also placed in the flask. From one to fifty equivalents of the phosphate employed (relative to the moles of either monomer employed) can be used, with twenty equivalents being the preferred quantity. To this mixture, a solvent is added; nonlimiting examples of solvents which can be employed include m-cresol, phenol, toluene, N-methylpyrrolidinone (NMP), diphenyl ether, tetrachloroethane or dimethylacetamide. Other solvents are possible, the primary requirement being that the growing polymer chains remain soluble in the phosphate/solvent mixture employed. In general, approximately one milliliter of solvent is used for each gram of monomer. For example, if a polymerization is initiated using approximately two grams of a bis(ketomethylene) compound and two grams of a bis(aminoketone), then approximately 4 milliliters of solvent is used. More or less solvent can be used if desired. The selection of the amount of solvent relates to the ease with which the polymerization solution may be stirred.

The mixture thus obtained is stirred and heated for between eighteen hours and five days at elevated temperature. The preferred temperature range is between 75° C. and 135° C., although lower or higher temperatures may be employed. Lower temperatures lead to slower, less convenient rates of polymerization, while higher temperatures tend to lead to lower molecular weights due to side reactions of monomers. The preferred reaction time depends greatly on the reaction temperature employed, the primary requirement for optimizing (e.g., maximizing) the polymer molecular weight being that the reaction be continued until no further increases in the viscosity of the polymerization solution are observed with time. For example, if the polymerization is run at a temperature of 100° C., seventy-two hours is a typical reaction time required to maximize the polymer molecular weight.

Isolation and purification of the polymers of the present invention can be accomplished by pouring the polymerization solution into a basic liquid phase designed to dissolve non-polymeric constituents of the polymer solution (e.g., the polymerization solvent, phosphate-containing species, and low molecular weight oligomers) while causing the polymer to precipitate. Non-limiting examples of liquid phases which can be used to accomplish this include various alcohols including methanol, ethanol, isopropanol, etc., and/or mixtures thereof. Water and/or mixtures of water with the above-mentioned alcohols may also be used. Bases dissolved in the liquid phase serve to neutralize the polymer as well as to form salts with (and thus render soluble) the phosphate species. A variety of bases can be employed, the primary requirement being that they are soluble in the liquid phase being employed as a non-solvent for the polymer. Non-limiting examples of bases which can be employed include ammonia, alkali metal carbonates and bicarbonates, and organic amines including triethylamine and pyridine.

Filtration of the resulting solution leads to isolation of the semi-purified polymer. Further purification of the polymer can be accomplished by (1) dissolving the polymer in a suitable solvent (toluene, NMP, etc.) followed by reprecipitation into a basic liquid phase such as those listed above, or (2) continuously extracting the polymer with a suitable solvent, such as an alcohol or water/alcohol mixture, or the like.

In a modification of the general procedure for preparing polymers of the present invention, nonlimiting examples of random copolymers which contain relatively small amounts of fluorine (for example, 1% to 5%) may be prepared as follows:

Two bis(ketomethylene) compounds (AA compounds) of the following general formula:

R'H₂C(CO)Y(CO)CH₂R', and a bis(aminoketone) compound (a BB compound) of the following general formula:

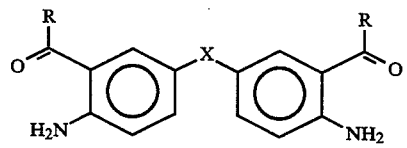

are placed in a round bottom flask, resin kettle, or other suitable vessel. For preparation of random copolymers of the type containing relatively small amounts of fluorine, it is required that .one of the two bis(ketomethylene) compounds contains either a 3F or a 6F group, and that the other does not. Preferably, the combined amounts of the two AA monomers are equimolar with respect to the total amount of the BB monomer.

For example, in the general structure (16) depicting a random copolymer, if n =0.2 m, then 20% of the bis(ketomethylene) AA monomers employed contain fluorine due to the presence of a 6F or a 3F group, and 80% of the bis(ketomethylene) AA monomers do not. Thus, if the fluorine containing AA monomer employed is 2,2'-bis[4-(4-acetylphenoxy)-phenyl] hexafluoropropane (e.g., Y is hexafluoroisopropylidene diphenoxy), and the non-fluorine containing bis(ketomethylene) AA monomer is 4,4-diacetyldiphenyl ether (e.g., W is an oxygen atom), and the bis(aminoketone) BB monomer is 3,3'-dibenzoyl-4,4'-diaminobiphenyl (e.g., X is nil), then the weight fraction of the fluorine in the copolymer is approximately 1.8%.

Detailed, non-limiting examples of the procedures which may be used to prepare polymers of the present invention are provided below:

EXAMPLE 4

Polymerization of 2,2'-bis[4-(4-acetylphenoxy)phenyl] hexafluoropropane and 3,3'-dibenzoyl-4,4'-diaminobiphenyl in a mixture of m-cresol and diphenyl phosphate to provide a polymer having the following repeating units:

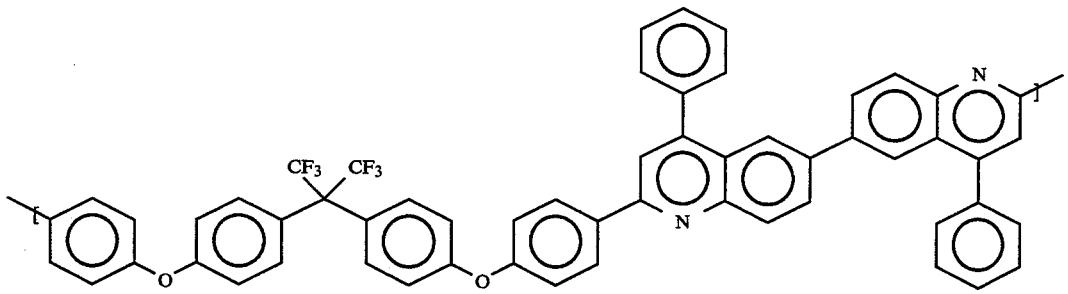

A solution containing 1.9999 grams (3.493 mmol) of 2,2'-bis[4-(acetyl-phenoxy)phenyl] hexafluoropropane, 1.3710 grams (3.493 mmol) 3,3'-dibenzoyl-4,4'-diaminobiphenyl, 4.1 milliliters of m-cresol and 21.85 grams of diphenyl phosphate was prepared by combining the reagents in a 100 milliliter 3 neck round bottom flask equipped with a reflux condenser, a nitrogen inlet and a mechanical stirrer. The mixture was heated to a constant temperature of approximately 90° C. with stirring. After approximately 72 hours, the polymer was precipitated by pouring the solution into a coagulation bath consisting of 90% anhydrous ethanol and 10% triethylamine. The polymer was isolated by filtration, redissolved in chloroform, and further purified by allowing it to reprecipitate by dripping the chloroform solution into a fresh coagulation bath consisting of ethanol/triethylamine. The polymer was collected by filtration, washed with anhydrous ethanol, and dried under vacuum at room temperature.

An IR analysis of the polymer showed no appreciable carbonyl absorption. The polymer was subsequently dissolved in toluene (approximately 10% by weight) and fabricated into a free standing film using a standard film casting technique. The film was subsequently shown to have a thermal onset of decomposition in a helium atmosphere at approximately 650° C. The dielectric constant of the film (8-12 GHz) was shown to be approximately 2.57. The dielectric constant was found to be very insensitive to humidity, in sharp contrast to polyimides. The polymer could be dissolved in N-methylpyrrolidinone to give a 10% by weight solution. This solution showed no changes after several months at room temperature in a sealed vial. Films of this polymer had tensile strengths of around 15 KPSI, and tensile moduli of around 400 KPSI, with elongations of about 6 to 8%.

The polymer was spin coated onto a silicon substrate and residual stress was measured using a bending beam apparatus. The residual stress after a thermal cycle of 25° C.-250° C.-25° C. was less than 10 MPa, while polyimides generally display about 40-50 MPa residual stress.

EXAMPLE 5

Polymerization of 2,2'-bis(4-acetylphenyl) hexafluoropropane and 3,3'-dibenzoyl-4,4'-diaminodiphenyl ether in a mixture of m- cresol and diphenyl phosphate to provide a polymer having the following repeating units:

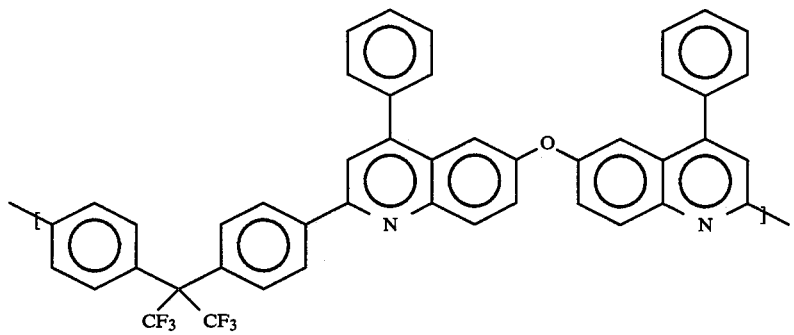

A solution containing 2.0000 grams (5.150 mmol) 2,2'-bis(4- acetylphenyl) hexafluoropropane and 2.1036 grams (5,150 mmol) 3,3'-dibenzoyl-4,4'-diaminodiphenyl ether, 6.04 grams m-cresol and 32.22 grams diphenyl phosphate was prepared by combining the reagents in a 100 milliliter 3 neck round bottom flask equipped with a reflux condenser, a nitrogen inlet and a mechanical stirrer. The mixture was heated to a constant temperature of approximately 90° C. with stirring. After approximately 72 hours, the polymer was precipitated by pouring the solution into a coagulation bath consisting of 90% anhydrous ethanol and 10% triethylamine. The polymer was isolated by filtration, redissolved in chloroform, and further purified by allowing it to reprecipitate by dripping the chloroform solution into a fresh coagulation bath consisting of 90% ethanol and 10% triethylamine. The polymer was collected by filtration, washed with anhydrous ethanol, and dried under vacuum at room temperature.

The polymer was shown to be soluble in chloroform, dichloromethane, toluene, 1,2-dichloroethane, N,N-dimethylacetamide and N-methylpyrrollidone. The polymer was shown to exhibit an onset of thermooxidative degradation (thermogravimetric analysis) at approximately 530° C. Upon fabrication into a free standing film employing standard film casting techniques, the polymer film was shown to have a density of 1,241 g/cc. The dielectric constant of the film sample averages 2.55 over the frequency range 8-12 GHz.

EXAMPLE 6

Polymerization of 2,2'-bis[4-(4-acetylphenoxy)phenyl hexafluoropropane and 3,3'-dibenzoyl-4,4'-diaminodiphenyl ether in a mixture of m-cresol and diphenyl phosphate to provide a polymer having the following repeating units:

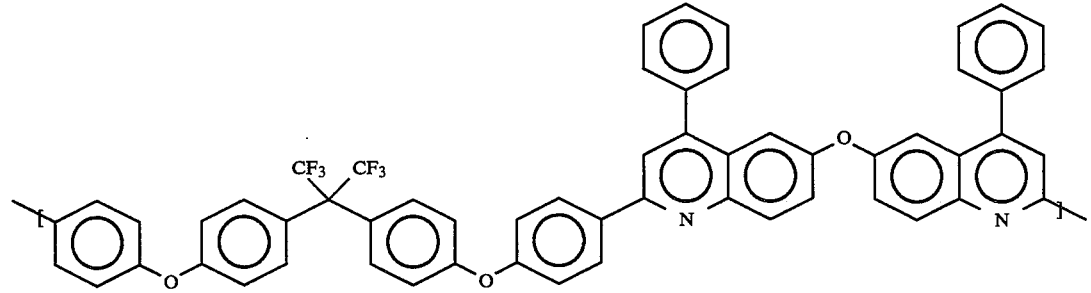

A solution containing 1.9999 grams (3,493 mmol) of 2,2'-bis[4-(4-acetylphenoxy) phenyl]hexafluoropropane, 1.4267 grams (3,493 mmol) 3,3'-dibenzoyl-4,4'-diaminodiphenyl ether, 4.1 milliliters m-cresol and 21.85 grams of diphenyl phosphate was prepared by combining the reagents in a 100 milliliter, 3-necked round bottom flask equipped with a reflux condenser, a nitrogen inlet and a mechanical stirrer. The mixture was heated to a constant temperature of approximately 90° C with stirring. After approximately 72 hours, the polymer was precipitated by pouring the solution into a coagulation bath consisting of 90% anhydrous ethanol and 10% triethylamine. The polymer was isolated by filtration, redissolved in chloroform, and further purified by allowing it to precipitate by dripping the chloroform solution into a fresh coagulation bath consisting of ethanol/triethylamine. The polymer was collected by filtration, washed with anhydrous ethanol, and dried under vacuum at room temperature until a constant weight was achieved.

EXAMPLE 7

Polymerization of 2,2′-bis (4-acetylphenyl) hexafluoropropane and 3,3′-dibenzoyl-4,4′ diaminobiphenyl in a mixture of m-cresol and diphenyl phosphate to provide a polymer having the following repeating units:

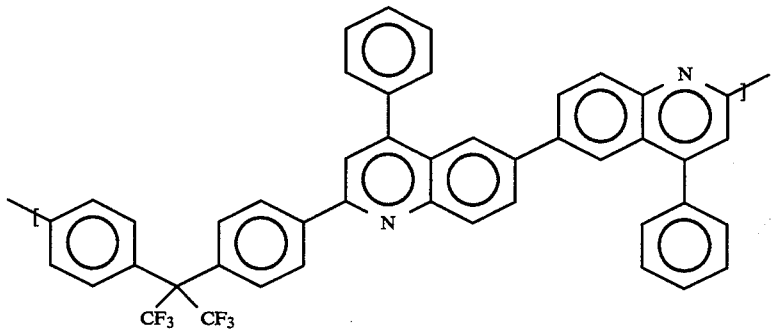

A solution containing 2.2703 grams (5.846 mmol) 2,2′-bis(4-acetylphenyl) hexafluoropropane and 2.2943 grams (5,846 mmol) 3,3′-dibenzoyl-4,4′-diaminobiphenyl, 6.86 grams m-cresol and 36.57 grams of diphenyl phosphate was prepared by combining the reagents in a 100 milliliter, 3-necked round bottom flask equipped with a reflux condenser, a nitrogen inlet and a mechanical stirrer. The mixture was heated to a constant temperature of approximately 90° C. with stirring. After approximately 72 hours, the polymer was precipitated by pouring the solution into a coagulation bath consisting of 90% anhydrous ethanol and 10% triethylamine. The polymer was isolated by filtration, redissolved in chloroform, and further purified by allowing it to precipitate by dripping the chloroform solution into a fresh coagulation bath consisting of ethanol/triethylamine. The polymer was collected by filtration, washed with anhydrous ethanol, and dried under vacuum at room temperature until a constant weight was achieved.

EXAMPLE 8

Polymerization of 1,1-bis[4-(4-acetylphenoxy) phenyl]-1-phenyl-2,2,2-trifluoroethane, and 3,3′-dibenzoyl-4,4 ′-diaminobiphenyl in a mixture of m-cresol and diphenylphosphate to provide a polymer having the following repeating units:

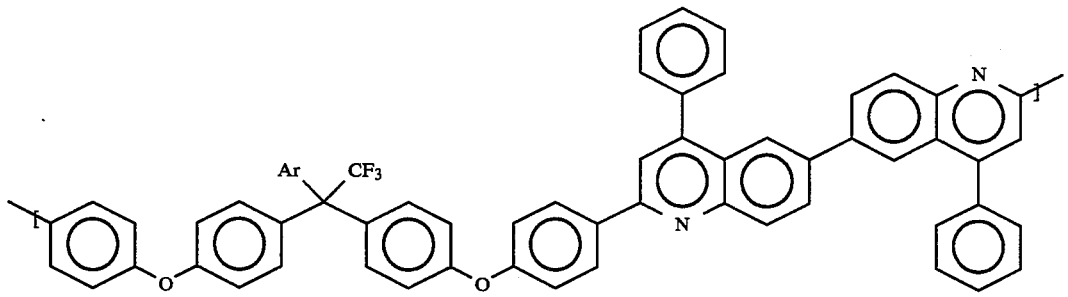

wherein Ar is phenyl.

A mixture of 100 grams (0.57 mol) of trifluoroacetophenone, 100 grams (0.7 mol) trifluoromethane sulfonic acid, and 100 grams (10.9 mol) anisole is stirred at room temperature for 24 hours. The mixture is then transferred to a separatory funnel and the organic material is washed with water (3×11), saturated bicarbonate (3×500 ml) and water (2×500 ml). The organic phase is dried and the volatiles removed in vacuo. The resulting material is crystallized from aqueous methanol. 37.2 grams (0.1 mol) of this product is refluxed with glacial acetic acid saturated with anhydrous hydrobromic acid. The mixture is cooled and poured over crushed ice and the solid collected. The crude material is recrystallized from ethanol and petroleum ether to give 1,1-bis(4-hydroxyphenyl)-1-phenyl-2,2,2-trifluoroethane.

A suspension of 16.9 grams (0.122 moles) anhydrous potassium carbonate in 373 milliliters of N,N′-dimethylacetamide is prepared in a 1 liter, 2-neck round bottom flask equipped with a reflux condenser and a nitrogen gas inlet. To the suspension is added 19.1 grams (0.0555 moles) of 1,1-bis(4-hydroxyphenyl)-1-phenyl-2,2,2-trifluoroethane using a powder addition funnel against a counter current of nitrogen gas. The system is purged and stirred under nitrogen for fifteen minutes, as heat is gradually applied via a heating mantle. Next, 20.21 milliliters (0.166 moles, 3 equivalents relative to the diphenol) of commercially obtained 4-fluoroacetophenone is added via a syringe to the heated solution. The solution is refluxed and stirred for 48 hours, at which time no diphenol is evident by thin layer chromatography. The quantity of solvent is reduced to approximately 200 milliliters by distillation, whereupon the solution is cooled, and poured into approximately 500 milliliters of 1 molar HCI The product precipitates as an off white granular solid. The crude product is distilled under reduced pressure to give polymer grade 1,1-bis[4-(4-acetylphenoxy)-phenyl]-1-phenyl-2,2,2-trifluoroethane.

A solution containing 1.846 grams (3.493 mmol) of 1,1-bis [4-(4-acetylphenoxy)phenyl]-1-phenyl-2,2,2-trifluoroethane, 1.3710 grams (3.493 mmol) 3,3'-dibenzoyl-4,4'-diaminobiphenyl, 4.1 milliliters of m-cresol and 21.85 grams of diphenyl phosphate is prepared by combining the reagents in a 100 milliliter 3 neck round bottom flask equipped with a reflux condenser, a nitrogen inlet and a mechanical stirrer. The mixture is heated to a constant temperature of approximately 90° C. with stirring. After approximately 72 hours, the polymer is precipitated by pouring the solution into a coagulation bath consisting of 90% anhydrous ethanol and 10% triethylamine. The polymer is isolated by filtration, redissolved in chloroform, and further purified by allowing it to reprecipitate by dripping the chloroform solution into a fresh coagulation bath consisting of ethanol/triethylamine. The polymer is collected by filtration, washed with anhydrous ethanol, and dried under vacuum at room temperature.

Solubility

The polymers of Examples 4–7 were all found to be soluble in chloroform, toluene, NMP and DMAC. In general, the fluorinated polymers of the present invention are more soluble than similar non-fluorinated polyquinolines. Commercially available fluorinated polyimides, such as polymers provided by DuPont, under the trademark "Avimid", and polymers provided by Ethyl Corporation, under the trademark "Eymyd H-20" are not soluble in organic solvents. These fluorinated polyimides are obtained from amic acid solutions, which are cyclized subsequent to casting or coating. Amic acid solutions are not stable indefinitely, and can present problems with reproducible curing. Preparation of high solids content solutions is important for applications where the polymer is deposited as a coating from solution, for example, spin coating or spraying.

Moisture Uptake

In general, the polymers of the present invention will have very low moisture uptake. Values as low as 0.15% moisture uptake at 75° C., 75% r.h. for 24 hr, and 0.3% moisture uptake after boiling in water for 24 hr, have been measured. Fluorinated polyimides do not provide such low moisture uptakes. For example, a polyamide 25 provided by Ethyl Corporation under the trademark Eymyd HP-20 ™ has a 1.5% moisture uptake at 75° F., 100% r.h. for 290 hr.

The polymers of Examples 4–7 have glass transition temperatures ($T_g$) ranging from 200° C. to 350° C. High $T_g$ polymers are desirable where high use temperatures are necessary and where further processing steps, such as soldering, require high temperatures.

The fluorinated polyquinolines of the present invention are distinguished by their combination of properties, which are not obtainable with other polymers. The incorporation of 3F and/or 6F groups enhances some properties, such as solubility, moisture uptake and dielectric constant, without degrading other properties such as mechanical strength or thermal stability.

The polyquinolines of the present invention have a wide variety of uses. The following examples of applications are intended to be illustrative and are in no way limiting. The instant polymers are useful in a broad range of electronics and microelectronics applications, including planarizing dielectric layers in integrated circuit manufacture, passivation layers, as protective coatings and potting compounds, as adhesives, for example as die attach adhesives, optionally with fillers, as resins for printed wiring board fabrication, for flexible circuit boards or wiring boards, as tape automated bonding substrates, as dielectric layers in multi-chip modules and other high density interconnect devices.

Referring to FIG. 1, a semi-schematic cross-sectional side view of a multi-chip module 10, provided in accordance with practice of the present invention, is shown. Such multi-chip module are wiring boards designed to hold several integrated circuit chips (IC's) (not shown) directly without the IC's first being packaged into individual chip carriers. The multi-chip module is typically (but not necessarily) fabricated using photolithographic techniques similar to those used in IC fabrication. The following procedure outlining multi-chip module fabrication is illustrative and many variations are known in the art and may be used with the present invention.

A substrate 12, typically a four- or six-inch silicon or alumina wafer having a plurality of resistors 13 on its surface, is spin-coated with a layer 14 of a fluorinated polyquinoline polymer provided in accordance with the present invention. Solvent from the spincoating process is removed in an oven, and the polyquinoline layer is cured by heating to a selected temperature for a selected period of time as described above to enhance the solvent resistance of the polyquinoline layer. Vias (not shown) are cut through the polymer by any of several techniques, for example, laser drilling or patterning and etching. A layer of metal 16, typically copper or aluminum, is deposited and patterned using techniques known in the art to form metal lines with a portion of the metal 16a extending through the via and contacting the resistors 13. A second layer of polyquinoline 18 provided in accordance with the present invention is spin-coated, dried and cured, completely covering the underlying metal. Vias are cut as above, and a second layer of metal is deposited and patterned. Additional layers of polymer 20 and metal 22 are added by repeating the above procedure. In some processes, it may be desirable to use adhesion promoters to enhance adhesion of the polymer to the silicon substrate or subsequent layers, or to plate the metal lines with chromium or gold before the application of the polymer.

The polymers of the present invention are also useful as dielectric materials in other passive or active discrete electronic components, such as capacitors, resistors, inductors, transformers, diodes, transistors and the like.

Figure 2:
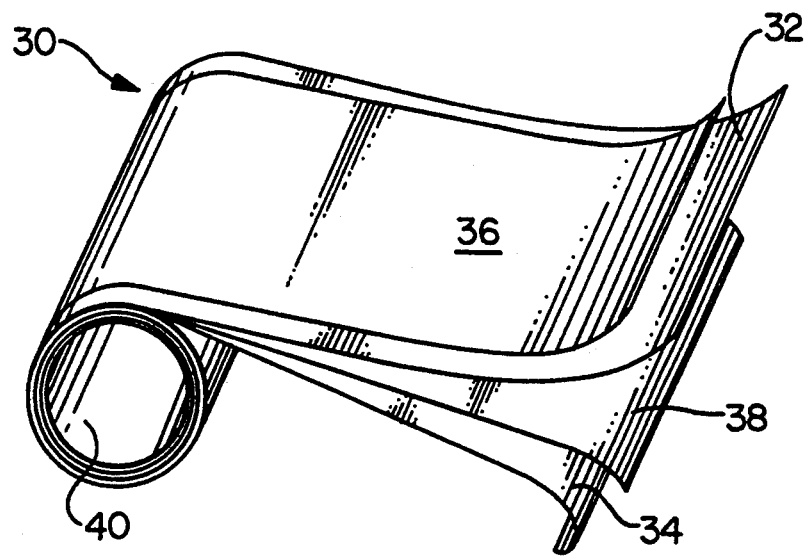
FIG. 2 is a semi-schematic exploded perspective view of a capacitor provided in accordance with the present invention.

Referring to FIG. 2, a semi-schematic exploded view of a capacitor 30 is shown. Dielectric films 32, and 34, comprising a fluorinated polyquinoline polymer provided in accordance with practice of the present invention, insulate metal foils 36, and 38, which form the plates of the capacitor. The multilayer structure is typically wound into a roll 40 and packaged after providing electrical connections (not shown).

The polymers of the present invention may also be used in coating applications such as liquid crystal displays, flat panel TV, light valves, solar windows, and the like. The instant polymers are also useful in optic and electro-optic applications such as optical wave guides, optical fibers, and non-linear optical devices. Electrical applications include wire coatings and wire wrap film, protective and anticorrosion coatings, as resin for connectors, housing, switches, plugs, sockets, or other molded electrical components.

The polymers of the present invention are also useful as resin for radomes, either as composites or unfilled polymer structures. The low dielectric constant and moisture uptake are advantageous in radome applications. The radome covers and protects the antenna and associated electronic radar receiving and transmitting equipment, while providing a window for electromagnetic radiation of the appropriate band. For certain aerospace applications, the high thermal stability of the instant polymers are also advantageous, for example, a radome on a leading wing edge.

Figure 3:
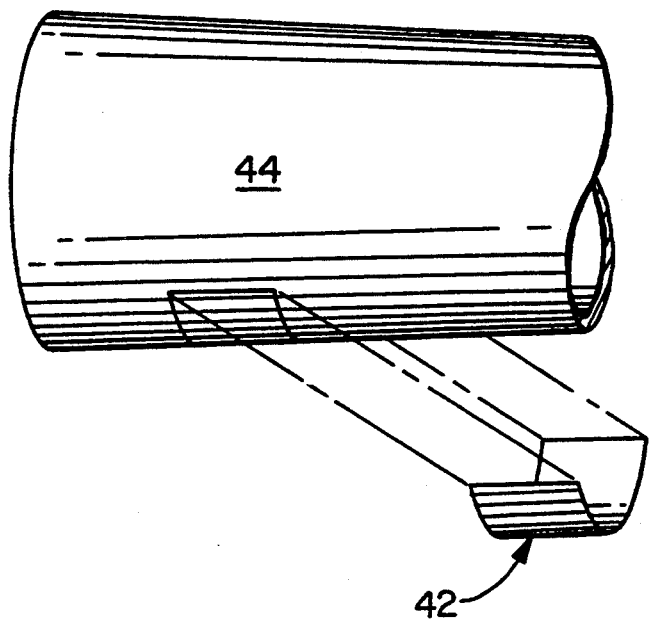
FIG. 3 is a semi-schematic perspective view of a radome provided in accordance with practice of the present invention mounted on the leading edge of an aircraft wing.

Turning to FIG. 3, there is shown a schematic view of a radome 42, comprising a fluorinated polyquinoline polymer provided in accordance with practice of the present invention, shaped as appropriate and mounted on a wing structure 44. The radome is essentially a radar transparent cover which is structurally self-supporting.

The fluorinated polyquinoline polymers of the present invention are also useful as coatings for spacecraft, where high transmission to visible light is desired. Coatings for use in other harsh environments, such as industrial, petrochemical, chemical, are also applications of the instant polymers.

The fluorinated polyquinoline polymers of the present invention may also be formed into fibers, by methods known in the art, such as wet spinning, dry spinning, and extrusion, and subject to further treatments such as hot or cold drawing.

Figure 4:
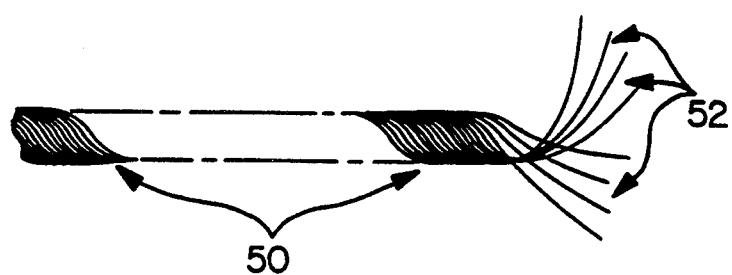
FIG. 4 is a semi-schematic perspective view of a multi-filament fiber provided in accordance with practice of the present invention.

Turning to FIG. 4, there is shown a semischematic view of a multi-filament fiber 50, comprising a plurality of mono-filaments 52 of a fluorinated polyquinoline polymer, provided in accordance with the present invention.

High strength, thermally stable films, optionally uniaxially oriented, may be prepared from the fluorinated polyquinoline polymers of the present invention.

Figure 5:
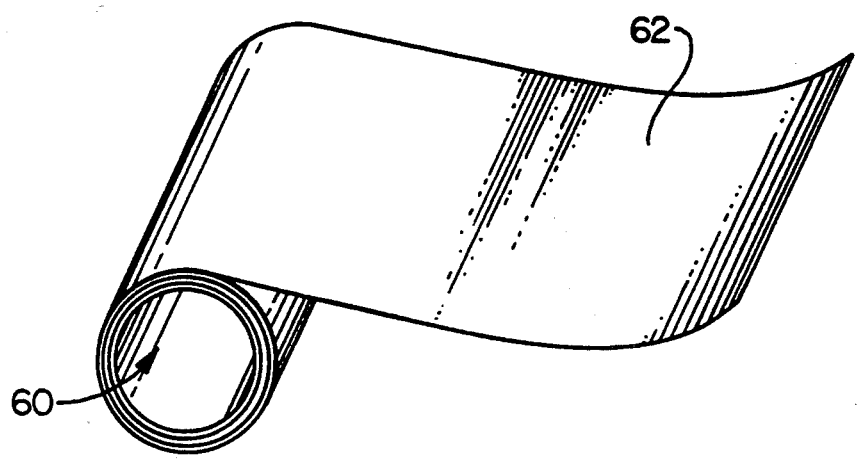
FIG. 5 is a semi-schematic perspective view of a roll of free-standing film provided in accordance with practice of the present invention.

Turning to FIG. 5, there is shown a roll 60 of freestanding film 62, formed from a fluorinated polyquinoline polymer prepared in accordance with practice of the present invention.

The above-described fibers and films have various uses, including textiles, cord, rope, fibers for use in composites, barrier films, bagging material, electrical and thermal insulation, and release films.

The polymers of the present invention may also be used as matrix resins for composites applications.

The above description of preferred embodiments of fluorinated polyquinoline polymers and the monomers useful for forming the polymers are for illustrative purposes. Because of variations which will be apparent to those skilled in the art, the present invention is not intended to be limited to the particular embodiments described above. The invention disclosed herein may suitably be practiced in the absence of any material or composition which is not specifically disclosed herein. The scope of the invention is defined in the following claims.

What is claimed is:

1. A monomer suitable for use in preparing fluorinated polyquinolines, the monomer having the formula:

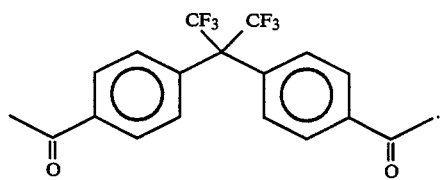

2. A monomer suitable for use in preparing fluorinated polyquinolines, the monomer having the formula:

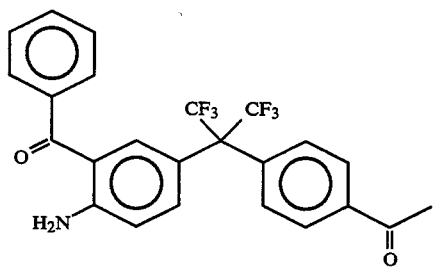

3. A monomer suitable for use in preparing fluorinated polyquinolines, the monomer having the formula:

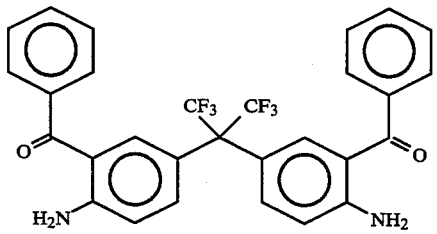

4. A monomer suitable for use in preparing fluorinated polyquinoline polymers, the monomer having the formula:

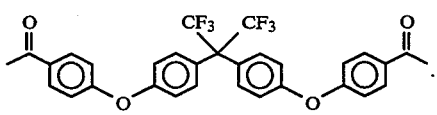

5. A monomer suitable for use in preparing fluorinated polyquinolines, the monomer having the formula:

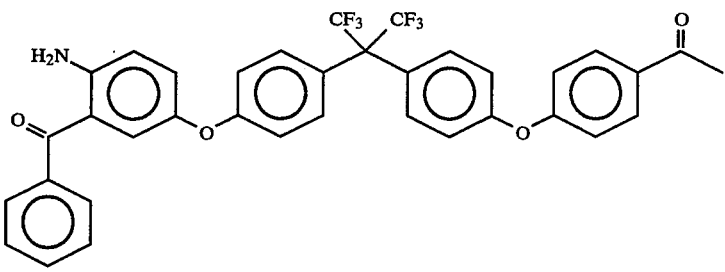
6. A monomer suitable for use in preparing fluorinated polyquinolines, the monomer having the formula:
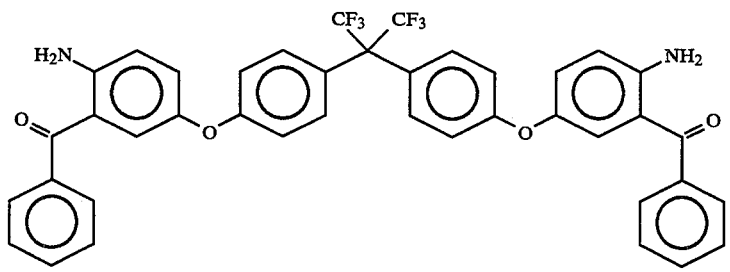
* * * * *

UNITED STATES PATENT AND TRADEMARK OFFICE
CERTIFICATE OF CORRECTION

PATENT NO. : 5,344,981
DATED : September 6, 1994
INVENTOR(S) : Neil H. Hendricks It is certified that error appears in the above-indentified patent and that said Letters Patent is hereby corrected as shown below:

On the Title Page, Item [56], References Cited, OTHER PUBLICATIONS, insert the following references:

```
    -- CA  97 ( 6): 39601z
       CA 101 (15): 130598r
       CA 113 (22): 202437k
       CA 115 (26): 281464j --;
```

Abstract, line 26, change "Ar40" to -- Ar' --.

Column 1, lines 6-10, after the title and before "RELATED APPLICATION" delete "This application is a division of U.S. Ser. No. 07/744,539, filed Aug. 13, 1991, now U.S. Pat. No. 5,247,050, which was a continuation-in-part of U.S. Ser. No. 07/568,059, filed Aug. 16, 1990, now abandoned."

UNITED STATES PATENT AND TRADEMARK OFFICE
CERTIFICATE OF CORRECTION

PATENT NO. : 5,344,981
DATED : September 6, 1994
INVENTOR(S) : Neil H. Hendricks It is certified that error appears in the above-indentified patent and that said Letters Patent is hereby corrected as shown below:

Column 1, line 11, after the title and before the "RELATED APPLICATION" section, insert the following text:

-- This invention was made, at least in part, with government support under National Aeronautics and Space Administration (NASA) Contract No. NAS1-18832. The United States Government has certain rights in this invention. --.

Column 1, line 56, change "polyamide" to -- polyimide --.

Column 4, line 26, change "tridluoroethylidene" to -- trifluoroethylidene --.

Column 8, line 31, change "Vol. 9,496" to -- Vol. 91 496 --.

Column 14, line 2, change "hours.-" to -- hours. --.

Column 14, line 14, change "1H" to -- $^1H$ --.

Column 16, line 22, change "R,R' X" to -- R,R',X --.

Column 20, line 46, change "3,493" to -- 3.493 --.

Column 21, line 54, change "5,846" to -- 5.846 --.

UNITED STATES PATENT AND TRADEMARK OFFICE
CERTIFICATE OF CORRECTION

PATENT NO. : 5,344,981
DATED : September 6, 1994
INVENTOR(S) : Neil H. Hendricks It is certified that error appears in the above-indentified patent and that said Letters Patent is hereby corrected as shown below:

Column 23, line 6, change "HCI" to -- HCl. --.

Column 23, line 55, change "polyamide" to -- polyimide --.

Column 23, line 56, before "provided" delete "25".

Signed and Sealed this

Sixth Day of June, 1995

Attest:

BRUCE LEHMAN

Attesting Officer

Commissioner of Patents and Trademarks